US007968529B2

(12) United States Patent
Nieuwenhuizen

(10) Patent No.: US 7,968,529 B2
(45) Date of Patent: Jun. 28, 2011

(54) USE OF SPHINGOLIPIDS FOR REDUCING HIGH PLASMA CHOLESTEROL AND HIGH TRIACYLGLYCEROL LEVELS

(75) Inventor: Willem Ferdinand Nieuwenhuizen, Bunnik (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 343 days.

(21) Appl. No.: 10/542,845

(22) PCT Filed: Jan. 20, 2004

(86) PCT No.: PCT/NL2004/000048
§ 371 (c)(1),
(2), (4) Date: Jul. 20, 2005

(87) PCT Pub. No.: WO2004/064820
PCT Pub. Date: Aug. 5, 2004

(65) Prior Publication Data
US 2006/0189575 A1    Aug. 24, 2006

(30) Foreign Application Priority Data

Jan. 20, 2003   (NL) .................................. 1022442
Oct. 6, 2003    (EP) .................................. 03078141

(51) Int. Cl.
*A61K 31/66*    (2006.01)
(52) U.S. Cl. .......................................... 514/75; 514/114
(58) Field of Classification Search ............ 514/75, 514/114
See application file for complete search history.

(56) References Cited

U.S. PATENT DOCUMENTS

| | | | |
|---|---|---|---|
| 5,190,876 A | 3/1993 | Kinkade, Jr. et al. | |
| 5,232,837 A | 8/1993 | Merrill, Jr. et al. | |
| 5,374,616 A | 12/1994 | Spiegel et al. | |
| 5,478,860 A | 12/1995 | Wheeler et al. | |
| 5,519,007 A * | 5/1996 | Della Valle et al. | 514/23 |
| 5,830,853 A | 11/1998 | Baeckstroem et al. | |
| 6,562,606 B1 | 5/2003 | Elias et al. | |
| 6,610,835 B1 | 8/2003 | Liotta et al. | |
| 6,713,057 B1 * | 3/2004 | Chatterjee | 424/94.6 |
| 2001/0011076 A1 | 8/2001 | Schwartz et al. | |
| 2002/0182250 A1 | 12/2002 | Hori et al. | |
| 2003/0049286 A1 | 3/2003 | Granger et al. | |
| 2003/0109044 A1 | 6/2003 | Logan et al. | |
| 2004/0047851 A1 | 3/2004 | Tabas et al. | |
| 2004/0063667 A1 | 4/2004 | Kishikawa et al. | |
| 2004/0147615 A1 | 7/2004 | Rinehart et al. | |
| 2004/0171557 A1 | 9/2004 | Iian et al. | |
| 2007/0098808 A1 * | 5/2007 | Sampalis | 424/523 |

FOREIGN PATENT DOCUMENTS

| | | |
|---|---|---|
| DE | 196 02 108 | 7/1997 |
| EP | 0373038 A | 6/1990 |
| EP | 0 988 860 | 3/2000 |
| EP | 1 291 340 | 3/2003 |
| EP | 1 452 181 | 9/2004 |
| FR | 2 492 259 A | 4/1982 |
| FR | 2 820 037 A | 8/2002 |
| JP | 61152632 A | 7/1986 |
| JP | 63 044842 A | 2/1998 |
| JP | 11 269074 A | 10/1999 |
| JP | 2000 350563 A | 12/2000 |
| JP | 2001 158735 A | 6/2001 |
| JP | 2001 158736 A | 6/2001 |
| JP | 2001 213858 A | 8/2001 |
| JP | 2002/068998 | 3/2002 |
| JP | 2002 226394 A | 8/2002 |
| JP | 2003 137894 | 5/2003 |
| KR | 2001 008 569 A | 2/2001 |
| WO | WO 92/03129 | 3/1992 |
| WO | WO 95/32002 | 11/1995 |
| WO | WO 97/11706 A | 4/1997 |
| WO | WO 99/41266 A | 8/1999 |
| WO | WO 99/61581 | 12/1999 |
| WO | WO 00/50574 | 8/2000 |
| WO | WO 01/60807 | 8/2001 |
| WO | WO 01/72701 | 10/2001 |
| WO | WO 02/34062 A | 5/2002 |
| WO | WO 02/102394 A | 12/2002 |
| WO | WO 03/011873 | 2/2003 |
| WO | WO 03/088761 | 10/2003 |
| WO | WO 03/096983 A | 11/2003 |
| WO | WO 2004/016257 | 2/2004 |
| WO | WO 2004/064819 | 8/2004 |

(Continued)

OTHER PUBLICATIONS

Eckhardt et al., "Dietary sphingomyelin suppresses intestinal cholesterol absorption by decreasing thermodynamic activity of cholesterol monomers", Gastroenterology, vol. 122, No. 4, pp. 948-956 (Apr. 2002), enclosed abstract.*

(Continued)

*Primary Examiner* — Kevin Weddington
(74) *Attorney, Agent, or Firm* — Weingarten, Schurgin, Gagnebin & Lebovici LLP

(57) ABSTRACT

The present invention is in the field of cholesterol and triglyceride-lowering methods and compositions. In particular, the present invention relates to the use of sphingolipids, more preferably phytosphingosine, sphingosine, sphinganine, ceramide, cerebroside and/or sphingomyelin for lowering the cholesterol and triglyceride levels in a subject and to the use of sphingolipids as a plasma and/or serum cholesterol and triglyceride lowering agent. The invention also encompasses methods of treatment of subjects suffering from high plasma cholesterol and triglyceride levels, as well as food items and supplements with increased sphingolipid levels.

14 Claims, 8 Drawing Sheets

FOREIGN PATENT DOCUMENTS

| | | |
|---|---|---|
| WO | WO 2004/064820 | 8/2004 |
| WO | WO 2004/064823 | 8/2004 |
| WO | WO 2004/096140 | 11/2004 |

OTHER PUBLICATIONS

Jiang, Xian-Cheng et al.: "Plasma sphingomyelin level as a risk factor for coronary artery disease" Arteriosclerosis Thrombosis and Vascular Biology, vol. 20, No. 12, Dec. 2000, pp. 2614-2618.

Leventhal, A. R. et al.: "Acid sphingomyelinase-deficient macrophages have defective cholesterol trafficking and efflux." The Journal of Biological Chemistry. Nov. 30, 2001, vol. 276, No. 48, pp. 44976-44983.

Chatterjee, Subroto: "Sphingolipids in atherosclerosis and vascular biology" Arteriosclerosis Thrombosis and Vascular Biology, vol. 18, No. 10, Oct. 1998, pp. 1523-1533.

Auge, Nathalie et al.: "Sphingomyelin metabolites in vascular cell signaling and atherogensis" Progress in Lipid Research, vol. 39, No. 3, May 2000, pp. 207-229.

Beers, M.H. and R. Berkow: "The Merck Manual of Diagnosis and Therapy, seventeenth edition" 1999, Merck Research Laboratories, Whitehouse Station, N.J., XP002311213 p. 1655, col. 1, paragraph 4-p. 1656, col. 1, paragraph 3.

Beers, M.H. and R. Berkow: "The Merck Manual of Diagnosis and Therapy, seventeenth edition" 1999, Merck Research Laboratories, Whitehouse Station, N.J., XP002341450 p. 1062; tables 148-4.

Bibel, D. J. et al.: "Antimicrobial Activity of Sphingosines" Journal of Investigative Dermatology, vol. 98, No. 3, 1992, pp. 269-273.

Bischoff, A. et al.: "Sphingosine-1-Phosphate and sphingosylphosphorylcholine constrict renal and mesenteric microvessels in vitro" British Journal of Pharmacology, Basingstoke, Hants, GB, vol. 130, No. 8, Aug. 2000, pp. 1871-1877.

Chong, P.H. et al.: "Atorvastatin calcium: an addition to HMG-CoA reductase inhibitors." Pharmacotherapy, vol. 17(6), pp. 1157-1177; 1997.

Chung, N. et al.: "Phytosphingosine as a specific inhibitor of growth and nutrient import in *Saccharomyces cerevisiae*." The Journal of Biological Chemistry. United States Sep. 21, 2001, vol. 276, No. 38, pp. 35614-35621.

Davaille et al. 2000. J. Biol. Chem., vol. 275, No. 44, pp. 34628-34633.

Fantini, J. et al.: "Synthetic Soluble Analogs of Galactosylceramide (GalCer) Bind to the V3 Domain of HIV-1 gp120 and Inhibit HIV-1-induced Fusion and Entry" Journal of Biological Chemistry, vol. 272, No. 11, 1997, pp. 7245-7252.

Howell et al. 2002. Current Organic Chemistry, vol. 6, No. 4, 2002, pp. 365-391.

Jung et al. 1996. Journal of Natural Products, vol. 59, No. 3, pp. 319-322.

Kim, et al. 2000. Phytotherapy Res., 14(6), 448-451.

Mei Jie et al.: "$C_2$—CEramide influences the expression and insulin-mediated regulation of cyclic nucleotide phosphodiesterase 3B and lipolysis in 3T3-I1 adipocytes." Diabetes, vol. 51(3), pp. 631-637; 2002.

Merrill Jr., A. H. et al.: "Role of dietary sphingolipids and inhibitors of sphingolipid metabolism in cancer and other diseases" Journal of Nutrition 1995 United States, vol. 125, No. 6 Suppl., 1995, pp. 1677S-1682S.

Ortenberg et al: Farmakologiya i Toksikologiya (Moscow), vol. 47, No. 4, 1984, pp. 102-105.

Rueda, R. et al.: "Addition of gangliosides to an adapted milk formula modifies levels of fecal *Escherichia coli* in preterm newborn infants" J. Pediatr., vol. 133, 1998, pp. 90-94.

Schmelz, E. M. et al.: "Sphingomyelin consumption suppresses aberrant colonic crypt foci and increases the proportion of adenomas versus adenocarcinomas in cf1 mice treated with 1,2-dimethylhydrazine: implications for dietary sphingolipids and colon carcinogenesis" Cancer Research, American Association for Cancer Research, Baltimore, MD, US, vol. 56, No. 21, Nov. 1, 1996, pp. 4936-4941.

Sosnowski et al. 1997. Journal of Urology, vol. 158, No. 1, pp. 269-274.

Sprong, R.C. et al.: "Bovine milk fat components inhibit food-borne pathogens." International Dairy Journal, vol. 12, pp. 209-215, 2002.

Thurman et al. 1994. Transplant Int.: Off. J. Eur. Soc. For Organ Transplantation. 1994, vol. 7 suppl 1, 1994, pp. s167-s170.

Turinsky J et al: "Effect of sphingoid bases on basal and insulin-induced glucose uptake by skeletal muscle", Journal of Cell Biology, vol. 115, No. 3 Part 2, 1991, p. 222A; & abstracts of papers presented at the thirty-first annual meeting of the american society for cell bi.

Van Veldhoven Paul P et al: "Do sphingoid bases interact with the peroxisome proliferator activated receptor alpha (PPAR-alpha)?" ; Cellular Signaling, vol. 12, No. 7, Jul. 2000, pp. 475-479, p. 477, col. 2, lines 13-29.

Vesper, H. et al.: "Sphingolipids in Food and the Emerging Importance of Sphingolipids to Nutrition" Journal of Nutrition, vol. 129, 1999, pp. 1239-1250.

Viola, G. et al.: "Absorption and distribution of arachidonate in rats receiving lysophospholipids by oral route" Journal of Lipid Research, Bethesda, MD, US, vol. 34, No. 11, 1993, pp. 1843-1852.

Yamada, T. et al.: "Growth inhibition of pancreatic cancer cells by sphingosylphosphorylcholine and influence of culture conditions" CMLS, Cell. mol. life. sci. vol. 53, pp. 435-441, 1997.

Zheng et al. 2002. Hepatology, vol. 36, No. 4 part 2, p. 215a. Abstract No. 196.

"Application for the Approval of Neptune Krill Oil™", Neptune Technologies and Bioressources, Summary Document, Sep. 2006, pp. 1-13.

"Oil Prepared from Antartic Krill (Euphasia Superba)-Neptune Krill Oil™" Ministry of Trade and Industry, January 2007, pp. 1-8.

Bunea et al., "Evaluation of the Effects of Neptune Krill Oil on the Clinical Course of Hyperlipidemia", Alternative Medicine Review, vol. 9 (4) 2004, pp. 420-428.

Willard, "Krill—The Master Oil", Syncronicity Magazine, Dec./Jan. 2005/06, pp. 20-21.

Duivenvoorden et al., "Dietary sphingolipids lower plasma cholesterol and triaclglycerol and prevent liver steatosis in *APOE*3Leiden mice$^{1-3}$", The American Journal of Clinical Nutrition, vol. 84 (3) 2006, pp. 312-321.

Eckhardt et al., "Dietary Sphingomyelin Suppresses Intestinal Cholesterol Absorption by Decreasing Thermodynamic Activity of Cholesterol Monomers", Gastroenterology 2002 (vol. 122), pp. 948-956.

Matsumoto et al., "Gene expression analysis on the liver of cholestyramine-treated type 2 diabetic model mice", Biomedicine & Pharmacotherapy, vol. 64 (2010), pp. 373-378.

Grigore et al., "Combination therapy in cholesterol reduction: focus on ezetimibe and statins", Vascular Health and Risk Management, vol. 4 (2) (2008), pp. 267-278.

van Vlijmen et al., "Apolipoprotein E*3-Leiden transgenic mice as a test model for hypolipidaemic drugs", Arzneimittelforschung, vol. 48 (4) (1998):396-402, Abstract, 1 pg.

Zadelaar et al., "Mouse Models for Atherosclerosis and Pharmaceutical Modifiers", Arterioscler. Thromb. Vasc. Biol., vol. 27 (2007), pp. 1706-1721.

* cited by examiner

USE OF SPHINGOLIPIDS FOR REDUCING HIGH PLASMA CHOLESTEROL AND HIGH TRIACYLGLYCEROL LEVELS

This application is a §371 national phase filing of PCT/NL2004/000048 filed Jan. 20, 2004; and claims priority to a Dutch application NL 1022442 filed Jan. 20, 2003, and to a European application EP 03078141.3 filed Oct. 6, 2003.

FIELD OF THE INVENTION

The present invention is in the field of cholesterol-lowering and triglyceride-lowering methods and compositions. In particular, the present invention relates to the use of specific sphingolipids, more preferably phytosphingosine, sphingosine, sphinganine, ceramide, cerebroside and/or sphingomyelin for lowering the cholesterol and triglyceride levels in a subject and to the use of sphingolipids as a plasma and/or serum cholesterol and triglyceride lowering agent.

BACKGROUND OF THE INVENTION

Cardiovascular diseases are caused by a number of synergistic factors of which elevated levels of cholesterol and triglycerides (triacylglycerol) in the blood are considered the most important. Cholesterol is an important building block for human and animal cells since is it one of the constituents of cellular membranes. The human cell is capable of synthesizing cholesterol, but cholesterol is also taken up from food sources. Both processes play an important role in cholesterol metabolism in humans.

Besides its essential function as building block of cellular membranes, cholesterol also plays a negative role in the occurrence of cardiovascular diseases (such as heart attack, seizure, and peripheral vascular diseases), in particular in relation to the occurrence of hardening of blood vessel walls (atherosclerosis). An elevated level of cholesterol especially in combination with elevated levels of triglycerides in the blood is the most important predictive (risk) factor for the occurrence of cardiovascular diseases and atherosclerosis.

In the blood cholesterol is transported in lipoproteins, which can be distinguished in a number of classes based on size and density. The very-low-density lipoproteins (VLDL), the intermediate-density lipoproteins (IDL), the low-density lipoproteins (LDL) and the high-density lipoproteins (HDL) being the most important.

Experimental and clinical research has shown that especially the amount of cholesterol transported by the VLDL, the IDL and the LDL form a risk factor for the occurrence of cardiovascular disease (the pro-atherogenic cholesterol). The HDL provides a protective effect on the occurrence of cardiovascular disease.

Randomized prospective clinical studies have shown that reduction of the plasma cholesterol and triglyceride level has a beneficial effect on the incidence of cardiovascular diseases and on the mortality as a result of these diseases. A provision is that this reduction is the result of a reduction in the pro-atherogenic cholesterol in VLDL, IDL and/or LDL. In order to treat and prevent cardiovascular disease in humans it is desired to reduce the level of the pro-atherogenic cholesterol, and to absolutely or relatively increase the proportion of the anti-atherogenic HDL.

In order to prevent and treat vascular and coronary disease in humans it is desired to lower LDL, and to increase the relative or absolute contribution of HDL.

In practice there are several possibilities to attain the desired reduction in plasma cholesterol. The main options being:
 a. inhibition of cholesterol synthesis;
 b. increasing the rate of cholesterol disposal (or its conversion products, primarily bile acids); and
 c. reducing the intake (absorption) of cholesterol and bile acids from the intestine.

Drugs that are currently applied for the inhibition of cholesterol synthesis or for the treatment of hypercholesterolemia target the enzyme hydroxymethyl-glutaryl-coenzyme A reductase (HMG-CoA reductase) the enzyme catalyzing the rate-limiting step in hepatic cholesterol synthesis. These HMG-CoA reductase inhibitors (or statins) are generally synthetic compounds that block the activity of the enzyme. Examples are simvastatin ("Zocor®"), pravastatin ("Pravachol®") and atorvastatin ("Lipitor®").

In order to increase the rate of cholesterol disposal bile acid-absorbing resins (e.g. cholestyramine, "Questran®") may be used. By the absorption of bile acids to these resins the secretion of bile acids in the feces increases and the resorption of bile acids from the intestinal lumen to the blood decreases which results in a shortage of bile acids in the body. This shortage is compensated by the body by an increased conversion of cholesterol into bile acids by the liver. In this way, cholesterol is disposed from the body in the form of bile acid.

Since the absorption of cholesterol from the intestinal lumen is in fact only possible when the cholesterol is kept in soluble form (suspension, solution, dispersion) in the lumen by, amongst others, bile acid, a reduction in the bile acid concentration in the intestine also results in a decreased absorption of cholesterol.

Medicaments that inhibit the (active) absorption of cholesterol from the intestinal lumen by inhibiting the cellular transport systems for cholesterol (and optionally other sterols) as present in the intestinal epithelium are largely in the developmental stage. One of those medicaments (Ezetimibe®) has recently become available in several countries, others are only used experimentally in the clinic.

Besides using medicaments, the above three goals may also be achieved by using other naturally occurring agents or agents derived from naturally occurring products (cf Hassel. 1998. Curr. Opin. Lipidol. 9:7-10). An example of a naturally occurring statin-containing preparation is the so-called red rice, a rice variety that carries a mould that naturally produces the metabolite lovastatin. This metabolite is similar to the cholesterol synthesis-inhibiting medicament lovastatin. Further, use may be made of for instance sterols that occur in plants, i.e. so-called phytosterols, to inhibit the uptake of bile acid and cholesterol from the intestine. This type of compounds now finds practical application in margarine products sold in the Netherlands under the brand names of "Benecol®" or "Becel Pro-actif®".

Despite the availability of the above agents, medicaments and compounds, there still exists a need for cholesterol lowering agents, in particular for use in the food industry, and preferably for human food products.

Besides lowering plasma cholesterol, lowering plasma triglyceride will also result in lower risk for cardiovascular diseases. Plasma triglyceride reductions can be achieved by administration of, for instance, Niacin which inhibits transport of fatty acids from adipose tissue to the liver for triglyceride synthesis and secretion into the circulation. Fibrates, such as Fenofibrate® and Bezofibrate®, also lead to lower plasma triglyceride levels. These drugs act via enhancement of the oxidation of fatty acids, thereby preventing the synthesis of triglycerides.

SUMMARY OF THE INVENTION

The present inventors have now surprisingly found that sphingolipids reduce both cholesterol and triacylglycerol levels of plasma in ApoE*3Leiden mice which represent a suitable animal model for studying the effect of drugs and food compounds on plasma cholesterol and triglyceride levels (Volger O L, van der Boom H, de Wit E C M, van Duyvenvoorde W, Hornstra G, Plat J, Havekes L M, Mensink R P, Princen H M G. Dietary plant stanol esters reduce VLDL-cholesterol secretion and bile saturation in apoE*3Leiden transgenic mice. Arterioscler Thromb Vasc Biol 2001; 21: 1046-1052; and Post S M, de Roos B, Vermeulen M, Afman L, Jong M C, Dahlmans V E H, Havekes L M, Stellaard F, Katan M B, Princen H M G). Cafestol increases serum cholesterol levels in apolipoprotein E*3-Leiden transgenic mice by suppression of bile acid synthesis (Arterioscler Thromb Vasc Biol 2000; 20: 1551-1556).

For example, apolipoprotein E*3-Leiden transgenic mice fed with a diet containing up to 1% sphingolipids (specifically phytosphingosine, sphingosine, sphinganine, ceramide, cerebroside and/or sphingomyelin) showed a dramatic reduction (up to 60%) in plasma cholesterol levels and an equally dramatic reduction (up to 50%) in plasma triglyceride levels, compared with control mice. As sphingolipids are natural compounds found in all eukaryotic cells, this paves the way for the preparation of foodstuffs and clinically safe medicaments without undesirable side effects, with a dual capacity to reduce TG (triglycerides) and cholesterol levels in a subject with a propensity for or suffering from a lipid-related disorder/disease.

In one aspect the invention now provides the use of a sphingolipid according to the formula (I)

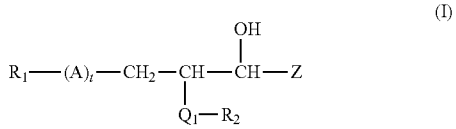

wherein
Z is $R_3$ or —CH(OH)—$R_3$;
A is sulphate, sulphonate, phosphate, phosphonate or —C(O)O—;
$R_1$ is H, hydroxyl, alditol, aldose, an alcohol, $C_1$-$C_6$ alkyl or amino acid;
$R_2$ is H or unsaturated or saturated ($C_1$-$C_{30}$) alkyl chain;
$R_3$ is unsaturated or saturated ($C_1$-$C_{30}$) alkyl chain;
$Q_1$ is a primary amine group (—$NH_2$), secondary amine group (—NH—) or an amide group (—NH—CO—); preferably an secondary amine group; and t is 0 or 1, or a precursor, a derivative or a pharmaceutically acceptable salt thereof for the manufacture of a medicament for reducing cholesterol and triglyceride levels in a subject. In a preferred embodiment, said sphingolipid is a sphingolipid according to the formula (II)

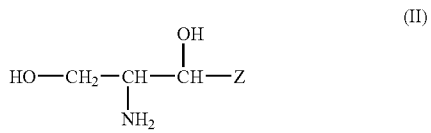

wherein

Z is $R_3$ or CH(OH)—$R_3$ and $R_3$ is an unsaturated or saturated ($C_1$-$C_{30}$) alkyl chain, even more preferably a sphingolipid according to formula (III)

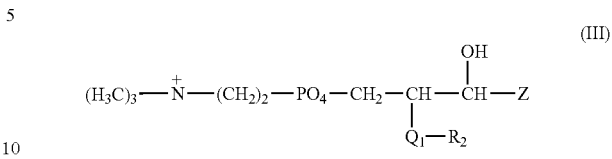

wherein
Z is $R_3$ or CH(OH)—$R_3$, preferably $R_3$, and $R_3$ is an unsaturated or saturated ($C_1$-$C_{30}$) alkyl chain, preferably $R_3$ is an unsaturated ($C_1$-$C_{30}$) alkyl chain;
$Q_1$ is a primary amine group (—$NH_2$), a secondary amine group (—NH—) or an amide group (—NH—CO—); preferably an amine group, and
$R_2$ is H or unsaturated or saturated ($C_1$-$C_{30}$) alkyl chain.

In highly preferred embodiments, wherein the sphingolipid is a sphingolipid according to the formula (II), a sphingolipid according to the present invention is phytosphingosine, sphinganine or sphingosine, and in another highly preferred embodiment, wherein the sphingolipid is a sphingolipid according to the formula (III), said sphingolipid is sphingomyelin.

Preferably said reduction in cholesterol and triglyceride levels comprises a reduction in plasma/serum cholesterol and triglyceride levels of said subject.

The present invention also provides use of a sphingolipid according to the formula (I), (II) or (III) or a precursor or a derivative as a plasma and/or serum cholesterol and triglyceride lowering agent in food products.

In another aspect, the present invention provides a method of lowering cholesterol and triglyceride levels in plasma and/or serum of healthy subjects comprising providing said subjects a diet with enhanced levels of a sphingolipid according to the formula (I), (I) or (III) or a precursor, a derivative or a pharmaceutically acceptable salt thereof.

In yet another aspect, the present invention provides a method of treatment of subjects suffering from high plasma cholesterol and triglyceride levels, said method comprising administrating to subjects in need thereof a therapeutically effective amount of a pharmaceutical composition, said composition comprising a sphingolipid according to the formula (I), (II) or (III), or a precursor, a derivative or a pharmaceutically acceptable salt thereof and a pharmaceutically acceptable carrier, and optionally one or more excipients.

DETAILED DESCRIPTION OF THE INVENTION

Figure 1:
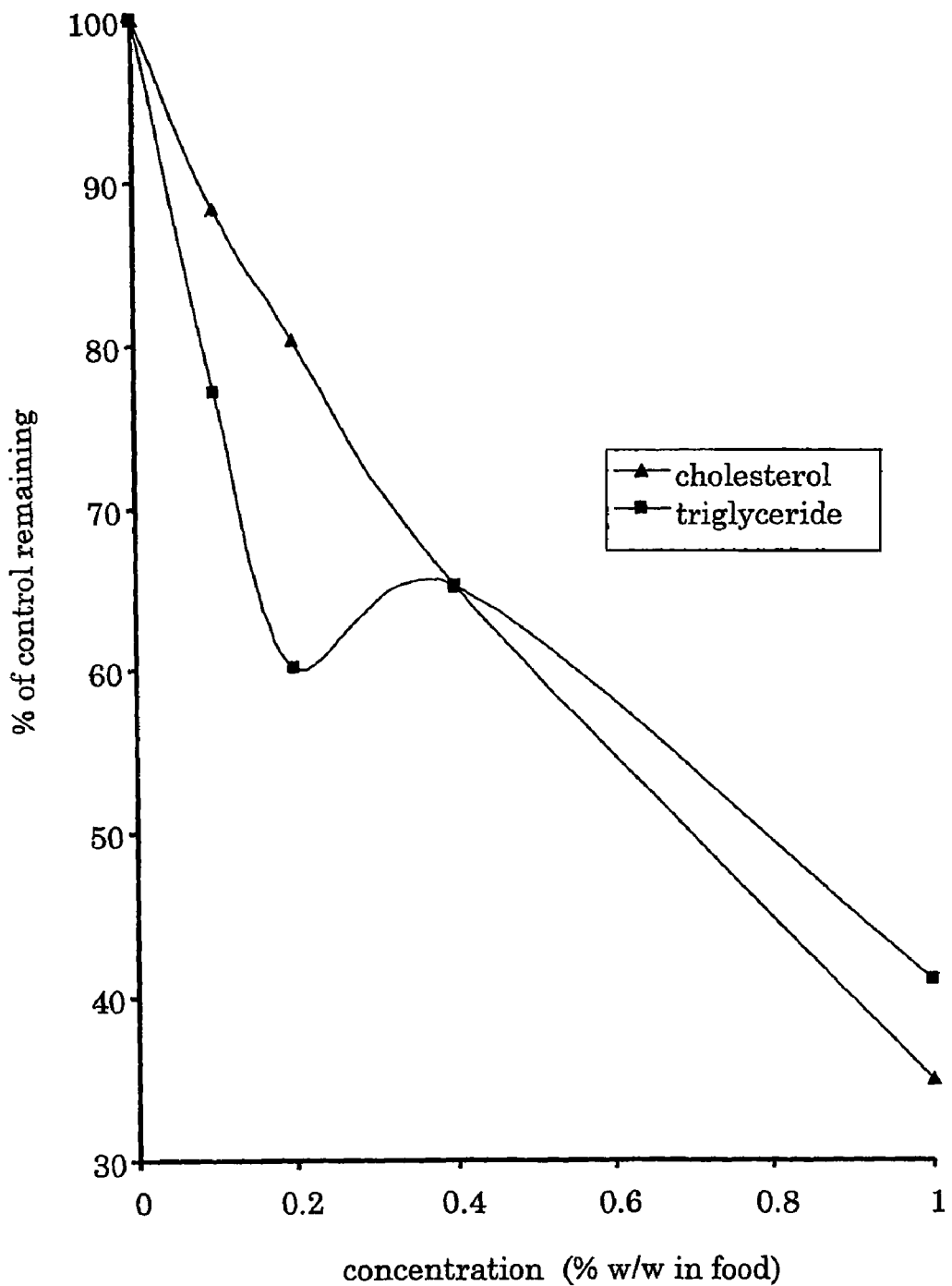
FIG. 1 shows the effect of increasing concentrations of phytosphingosine on plasma cholesterol and triglyceride concentrations, expressed as % of the concentrations in the control group.
Figure 2:
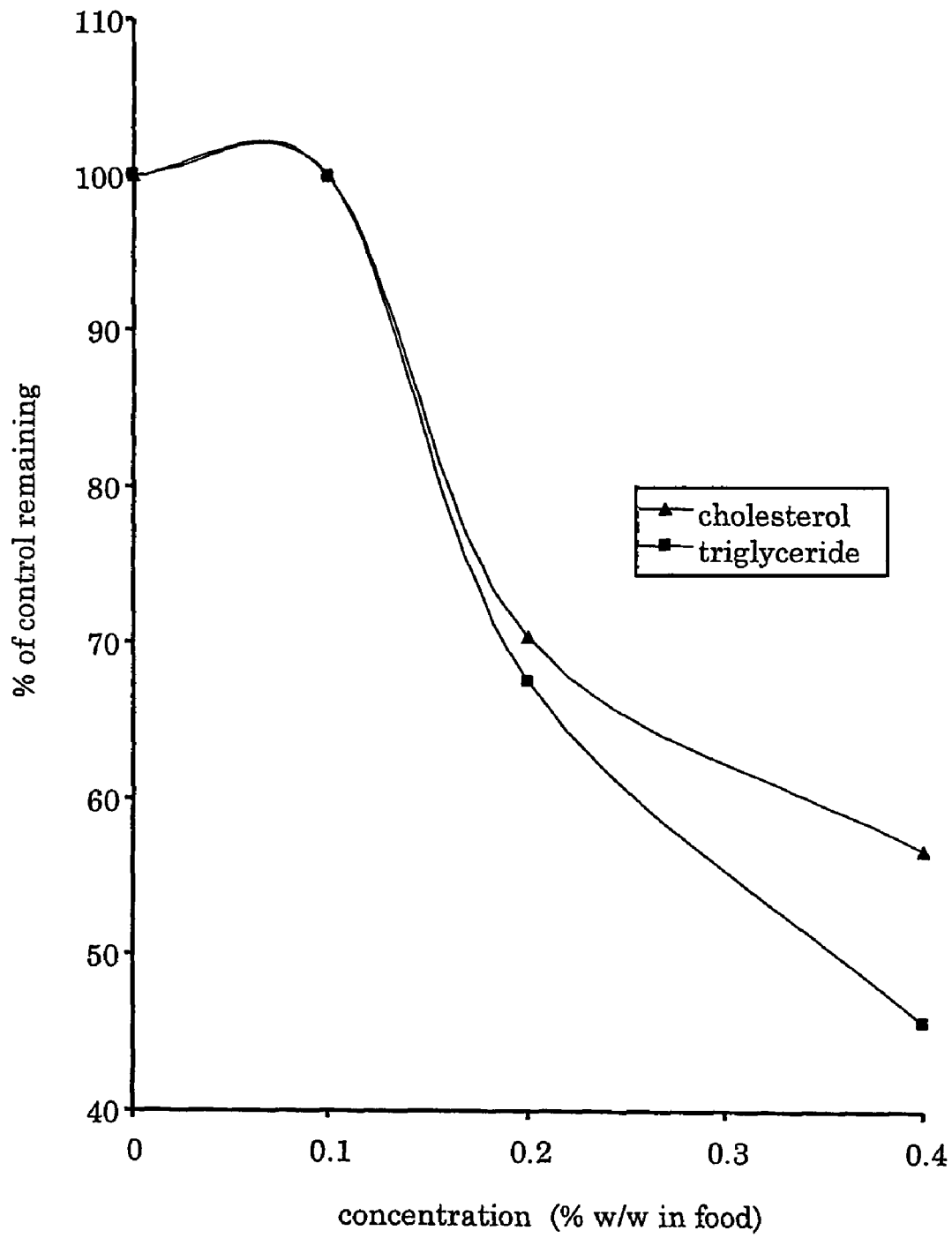
FIG. 2 shows the effect of increasing concentrations of sphingosine on plasma cholesterol and triglyceride concentrations, expressed as % of the concentrations in the control group.
Figure 3:
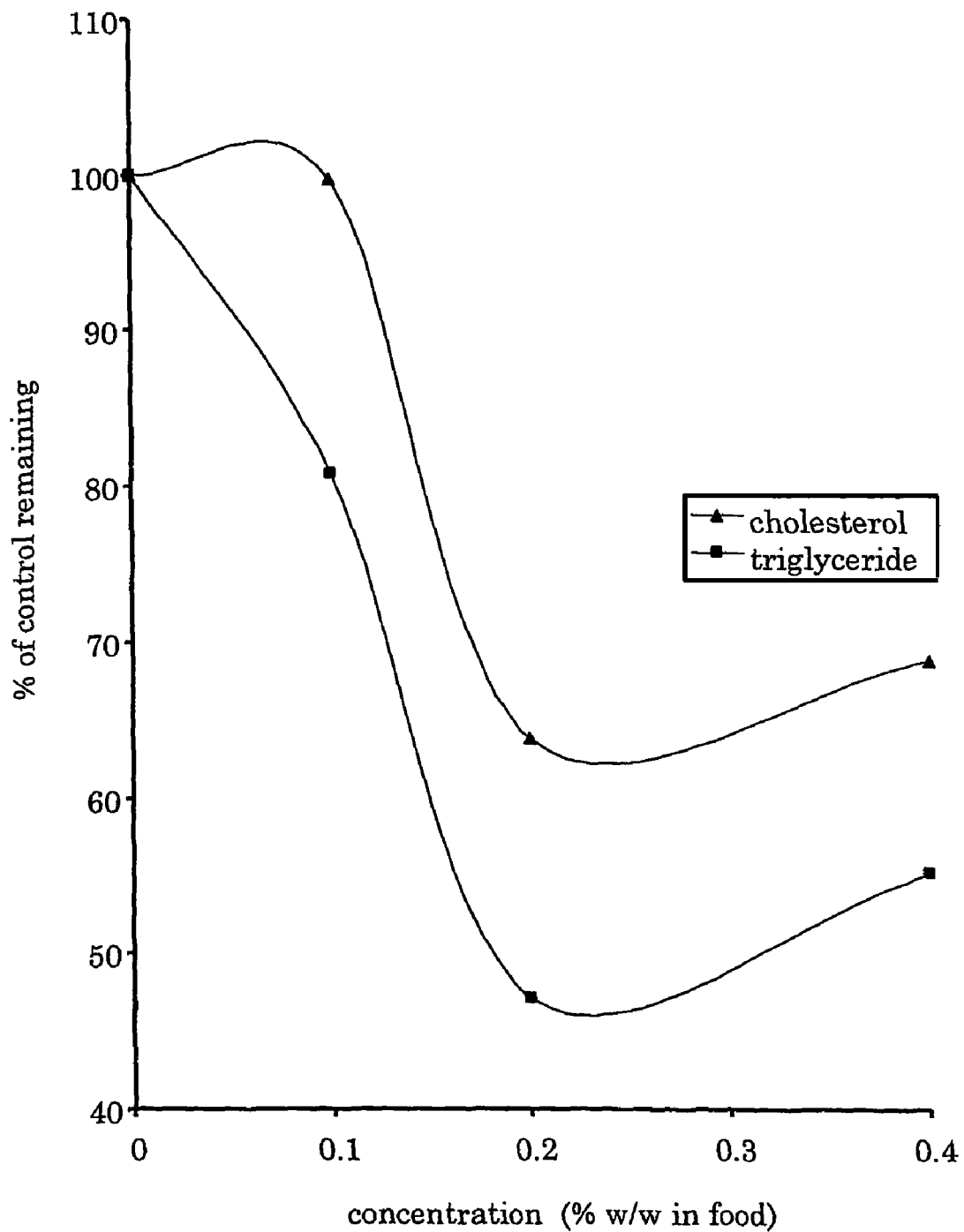
FIG. 3 shows the effect of increasing concentrations of sphinganine on plasma cholesterol and triglyceride concentrations, expressed as % of the concentrations in the control group.
Figure 4:
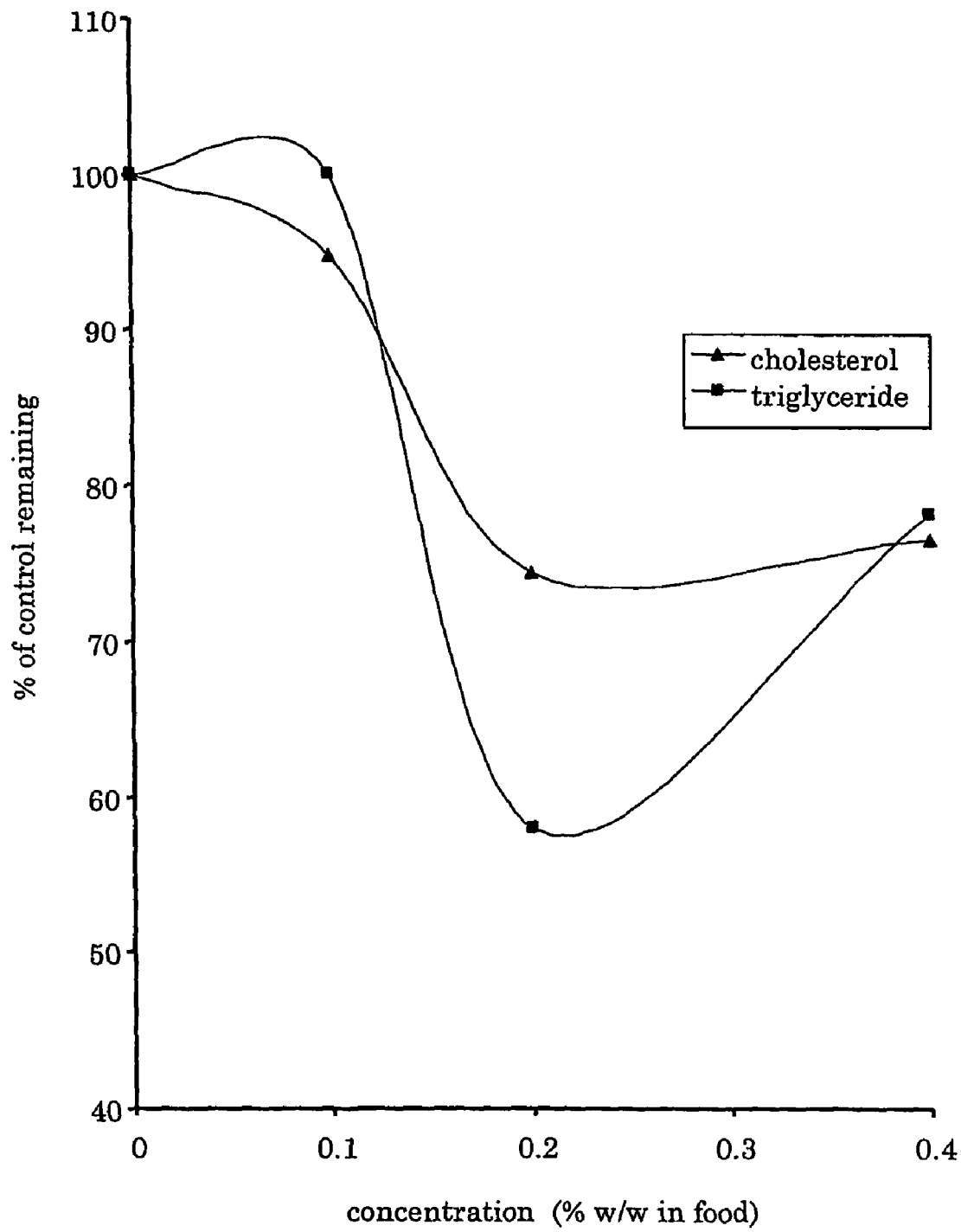
FIG. 4 shows the effect of increasing concentrations of cerebroside on plasma cholesterol and triglyceride concentrations, expressed as % of the concentrations in the control group.
Figure 5:
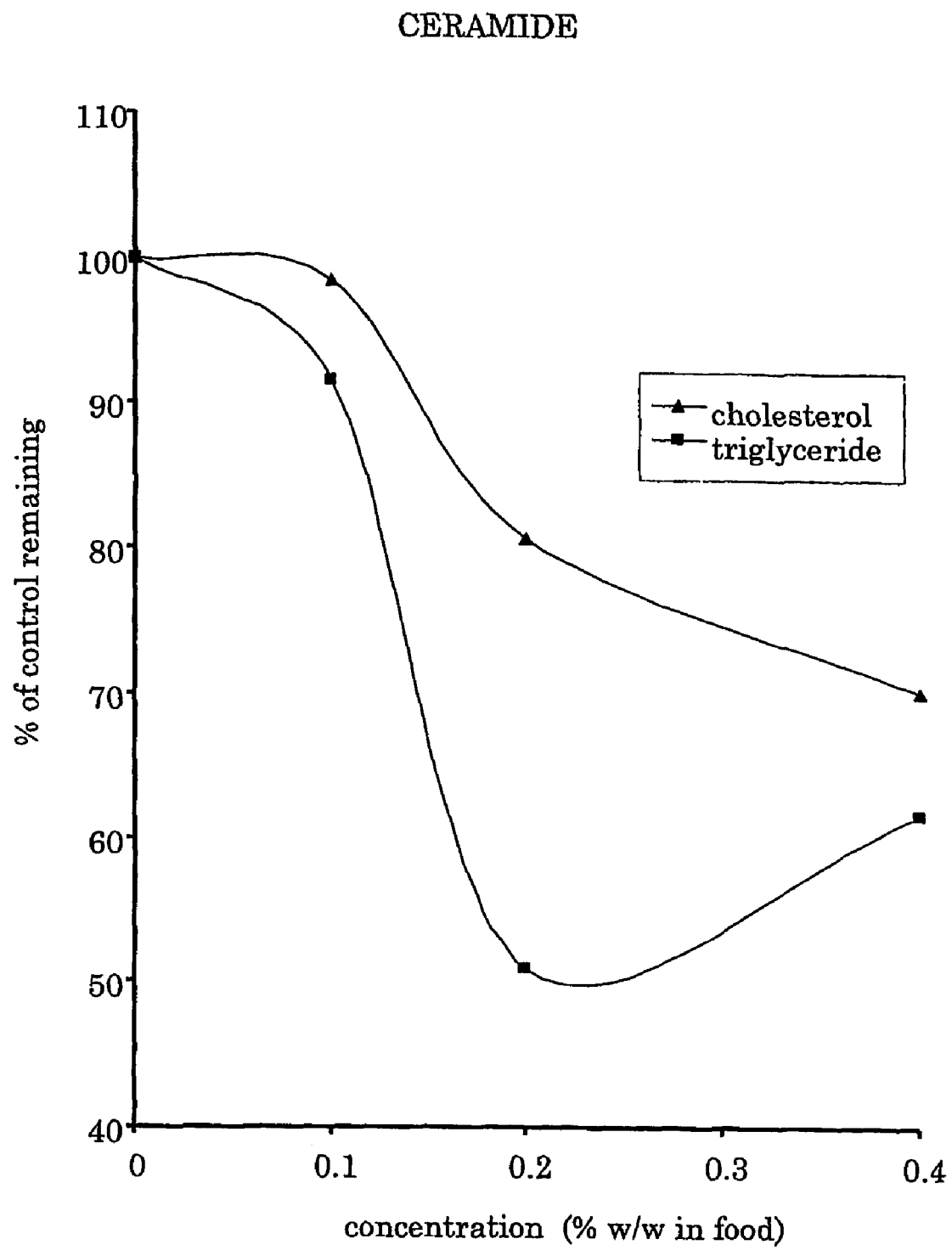
FIG. 5 shows the effect of increasing concentrations of ceramide on plasma cholesterol and triglyceride concentrations, expressed as % of the concentrations in the control group.
Figure 6:
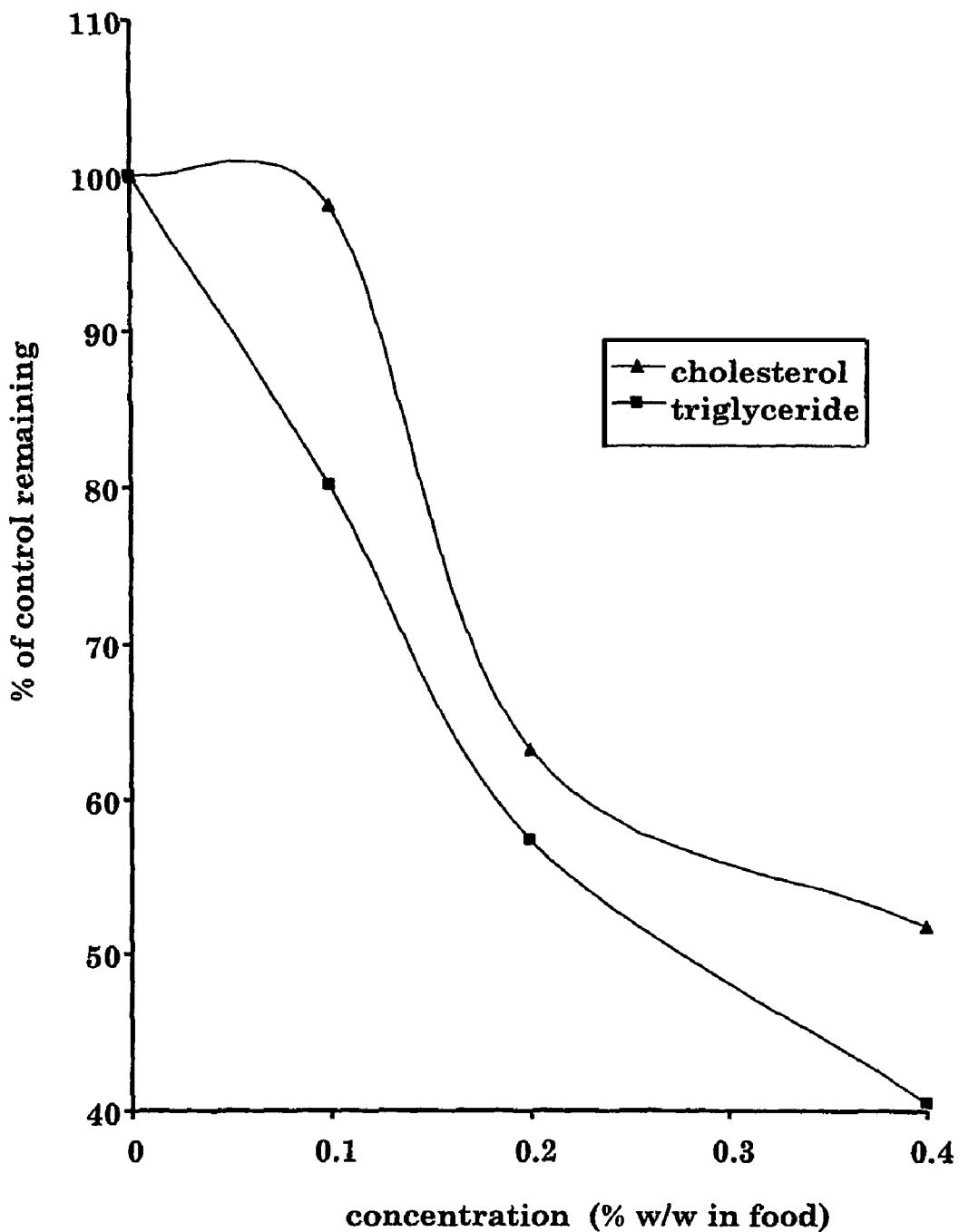
FIG. 6 shows the effect of increasing concentrations of sphingomyelin on plasma cholesterol and triglyceride concentrations, expressed as % of the concentrations in the control group.

The term "plasma" as used herein, is the watery, non-cellular portion of the blood from which cellular components, such as red and white blood cells, have been removed usually by centrifugation.

The term "serum" as used herein, is the watery, non-cellular portion of the blood that is left after blood has been clotted and the solids have been removed. Clotting removes blood cells and clotting factors. Serum is thus essentially the same as plasma except that, additionally, clotting factors such as fibrinogen have been removed. Serum and plasma, being watery, contain water-soluble (hydrophilic) substances such as water-soluble vitamins, carbohydrates, and proteins.

As used herein, the term "sphingolipid" includes the generally accepted term of this particular fat-like compound, but it is specifically used to address the group of compounds according to the formulas (I), (II) and (III) of the present invention, including analogs or derivatives or pharmaceutically acceptable salts thereof, alone, or in combination, or as a so-called precursor compound, unless explicitly noted otherwise.

The term "elevated amount" (or "increased amount") relates to an amount of a component in a composition that is higher than the amount of component in the composition in nature or without human intervention. The elevated amount of a component can be caused by addition of a component to a composition which normally does not contain said component, i.e. by enrichment of the composition with said component. An elevated amount of a component can also be caused by addition of a component to a composition which already contains said component, but which has, when the component is added, concentrations of the component which normally do not occur. Also this is called enrichment of the composition with the component.

Because of the variations in the amounts of sphingolipids (such as phytosphingosine, sphingosine, sphinganine, sphingomyelin, ceramide, cerebroside and lyso-sphingomyelin in different foodstuffs no general values can be given for the amounts which will be indicated as "elevated amounts" according to the invention. For instance, a small amount of sphingomyelin in potato will be easily called an "elevated amount", because potato from itself does hardly contain any sphingomyelin. The same amount in milk, which normally does contain relatively high concentrations of sphingomyelin, will not give rise to the denomination of "elevated amount".

The term "therapeutically effective amount" as used herein refers to an amount of a therapeutic agent to treat, ameliorate, or prevent a desired disease or condition, or to exhibit a detectable therapeutic or prophylactic effect. The precise effective amount needed for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation.

A "derivative", "analog" or "analogue" is defined herein as a sphingolipid according to the formula (I), (II) or (III) that is subjected to a (bio)chemical modification (e.g. organo-chemical or enzymatical). Derivatising may comprise the substitution of certain chemical groups to the sphingolipid, thereby retaining the sphingolipid character of the compound. Such derivatizations are known in the art. The derivatives and analogues maintain the biological activity of the natural sphingolipid and act in a comparable way, but may provide advantages to the molecule such as longer half-life, resistance to degradation or an increased activity. A very suitable derivative for phytosphingosine is for instance TAPS (see below). Such a derivative may suitably be used in embodiments of the present invention since after hydrolysis, for instance in the body, the converted compound will exert its cholesterol and triglycerides lowering effect.

A "pharmaceutically acceptable salt" is defined herein as a salt wherein the desired biological activity of the sphingolipid is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base addition salts formed with metal cations such as zinc, calcium, bismuth, barium, magnesium, aluminium, copper, cobalt, nickel, cadmium, sodium, potassium and the like, or with a cation formed from ammonia, N,N-dibenzylethylene-diamine, D-glucosamine, tetraethylammonium or ethylenediamine; or (c) combinations of (a) and (b); e.g. a zinc tannate or the like. The use of a pharmaceutically acceptable salt of a sphingolipid according to the formula (I), (II) or (III), such as an ammonium salt or a chloride salt is preferred since the salt form is better soluble and will thus enhance the bio-availability of the sphingolipid. Preferably a salt of HCl is used. The use of a pharmaceutically acceptable salt is not limited to pharmaceutical preparations, but includes the use in food items or food supplements.

A "precursor" is defined herein as a derivative of the active compound with similar, less or no activity, and which can be transformed to the active compound e.g. by the digestive tract or other digestive systems in the body. Such precursors can be obtained by chemical or enzymatic modification of the active molecule.

"Subject" as used herein includes, but is not limited to, mammals, including, e.g., a human, non-human primate, mouse, pig, cow, goat, cat, rabbit, rat, guinea pig, hamster, horse, monkey, sheep, or other non-human mammal; and non-mammal animals, including, e.g., a non-mammalian vertebrate, such as a bird (e.g., a chicken or duck) or a fish, and an invertebrate.

Sphingolipids are lipids of which some occur in food in low concentrations and which form a minor but important constituent of the cells of plants, animals and man. Since several sphingolipids occur naturally in the body of man and animal, they will be easily acceptable for addition to food compounds or as pharmaceutical agents.

Sphingolipids are generally composed of a long sphingoid base (sphingosine, sphinganine, phytosphingosine, or a related compound) as the central group of the molecule or "backbone" (see intra alia Karlsson. 1970. Chem. Phys. Lipids, 5:6-43), which comprises an amide-linked long-chain fatty acid and a head group. There are hundreds of known classes of sphingolipids with different head groups (e.g. cholinephosphate, glucose, galactose, polysaccharides) and with different fatty acids and sphingoid bases (see intra alia Merrill & Sweeley. 1996. New Comprehensive Biochemistry: Biochemistry of Lipids, Lipoproteins, and Membranes, (Vance, D. E. & Vance, J. E., eds.), pp. 309-338, Elsevier Science, Amsterdam).

The simplest sphingolipids, like sphingosine and sphinganine normally occur in food in very low concentrations. The richest sources of sphingolipids are dairy products, eggs, meat and soy beans. The most abundant sphingolipids in our food are sphingomyelin (milk and eggs) and ceramide (meat). Whole milk contains predominantly sphingomyelin, but also contains glucosylceramide, lactosylceramide and gangliosides. Potato, apple, tomato, spinach, pepper and rice especially contain cerebrosides in low concentration (see, e.g. Stryer L., Biochemistry, [W.H. Freeman and Co., NY, USA[, 1988, p. 287 and Ryu J, Kim J S, Kang S S., Cerebrosides from Longan Arillus. Arch Pharm Res. 2003 February; 26(2): 138-42; Kawatake S, Nakamura K, Inagaki M, Higuchi R. Isolation and structure determination of six glucocerebrosides from the starfish Luidia maculata. Chem Pharm Bull (Tokyo) 2002 August; 50(8):1091-6).

It is known that sphingosine and sphingosine-analogs inhibit growth and metastasis of human and animal tumor cells (see e.g. EP 0 381 514). It is also known that administration of sphingomyelin to the food of rats can significantly decrease the chances of occurrence of malignant, chemically induced colon cancer (see Schmeltz, E., et al.).

Sphingolipids are also used in pharmaceutical compositions to protect skin and/or hair against the damaging effects of air pollution (see e.g. U.S. Pat. No. 5,869,034).

The antimicrobial action of sphingosine as a component of the skin against bacteria such as Staphylococcus aureus, Candida albicans and Propionibacterium acnes is known from dermatology (Bibel et al. 1992. J. Invest. Dermatol. 98(3): 269-73; Bibel et al. 1995. Clin Exp Dermatol 20(5):395-400), and the application of topical ointments comprising sphingosine is described therein.

The present inventors have now found that sphingolipids can be used to lower cholesterol and triglyceride levels in a subject when such a sphingolipid is administered to said subject as, for instance, a food supplement or medicament.

The present invention in a first aspect relates to the use of a sphingolipid or a precursor, a derivative or a pharmaceutically acceptable salt thereof with the general formula:

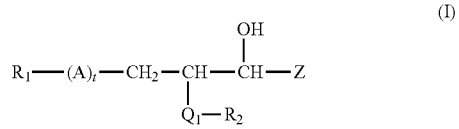

(I)

wherein
Z is $R_3$ or —CH(OH)—$R_3$;

A is sulphate, sulphonate, phosphate, phosphonate or —C(O)O—;
$R_1$ is H, hydroxyl, alditol, aldose, an alcohol, $C_1$-$C_6$ alkyl or amino acid;
$R_2$ is H or unsaturated or saturated ($C_1$-$C_{30}$) alkyl chain;
$R_3$ is unsaturated or saturated ($C_1$-$C_{30}$) alkyl chain;
$Q_1$ is a primary amine group (—$NH_2$), a secondary amine group (—NH—) or an amide group (—NH—CO—); and
t is 0 or 1,
for the manufacture of a medicament for reducing cholesterol and triglyceride levels in a subject.

$R_1$ can be selected from aldose radicals such as radicals of acesulfam, allose, altrose, arabinose, erythrose, fructose, fucose, galactose, glucose, gulose, idose, isomaltose, lactose, lyxose, maltose, mannose, melezitose, psicose, raffinose, rhamnose, ribose, saccharose, sorbose, stachyose, sucrose, tagatose, talose, threose, trehalose, turanose, xylose and xylulose, and other mono-, di-, or polysaccharides.

$R_1$ is preferably selected from amino acids radicals, such as radicals of alanine, arginine, asparagines, aspartate, carnitine, citrulline, cysteine, cystine, GABA, glutamate, glutamine, gluthathione, glycine, histidine, hydroxyproline, isoleucine, leucine, lysine, methionine, ornithine, phenylalanine, proline, serine, taurine, threonine, tryptophane, tyrosine and valine or derivatives or combinations thereof.

$R_1$ is more preferably selected from the group consisting of hydrogen, hydroxyl or hydroxyl-containing group (e.g. hydroxyalkyl), alditol radical or polyol radical, such as radicals of adonitol, arabitol, dulcitol, erythritol, ethyleneglycol, glycerol, inositol, lactitol, maltitol, mannitol, propyleneglycol, ribitol, sorbitol, threitol and xylitol, and of methanol, ethanol, ethanediol, isopropanol, n-propanol, 1,3-propanediol, and other poly-alcohols.

Even more preferably $R_1$ is selected from the group consisting of radicals of alcohols such as, choline, ethanolamine, ethanol, glycerol, inositol, tyrosine and serine and still more preferably from the alcohol moieties of phosphoglycerides or phosphoglyceride-alcohols, such as choline, serine, ethanolamine, glycerol or inositol.

$R_1$ is most preferably a hydroxyl group.

(A) can have any desired counter-ion for the formation of a salt of a sphingolipid according to the formula (I).

It is possible that the amino group such as may be present in the form of $Q_1$ in a sphingolipid according to the formula (I) is modified, e.g. by single or multiple methylation, alkylation, acylation of acetylation or by modification to a formic acid amide.

Also the free hydroxyl groups in the formula (I), specifically those in $R_3$ may be modified in ways known to the skilled person.

Further, all possible racemates and (dia)stereoisomers of a sphingolipid according to the formula (I) can be used in the present invention. It is possible to use compounds according to the formula (I) wherein $Q_1$ is substituted by e.g. H, a hydroxyl, a carboxyl or a cyano group. Preferred is a compound wherein $Q_1$ is the amino group.

$R_2$ is H or unsaturated or saturated ($C_1$-$C_{30}$) alkyl chain and $R_3$ is unsaturated or saturated ($C_1$-$C_{30}$) alkyl chain.

The term alkyl as used herein refers to a saturated or unsaturated straight chain, branched or cyclic, primary, secondary or tertiary hydrocarbon of $C_1$-$C_{30}$, optionally substituted, and comprises specifically methyl, ethyl, propyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl and 2,3-dimethylbutyl, heptyl, octyl, nonyl, decyl, undecyl, dodecyl, tridecyl, tetradecyl, pentadecyl, hexadecyl, heptadecyl, octadecyl, nonadecyl, eikosyl, heneikosyl and dokosyl and isomers thereof.

The $C_1$-$C_{30}$ alkyl chain or -group may be optionally substituted with one or more groups selected from the collection consisting of hydroxyl, amino, alkylamino, arylamino, alkoxy, aryloxy, nitro, cyano, sulphonic acid, sulphate, sulphonate, phosphonate or phosphate, either unprotected or protected insofar as desired. These substitutes are known to the person skilled in the art, for example from Greene et al., Protective Groups in Organic Synthesis, John Wiley & Sons, $2^{nd}$ Edition, 1991. Preferred embodiments of $C_1$-$C_{30}$ alkyl chains constitute $C_8$-$C_{24}$ alkyl chains.

A compound of the formula (I) is a sphingolipid, or a precursor, a derivative or pharmaceutically acceptable salt thereof.

Even more preferably, in a compound according to the formula (I), or a precursor, a derivative or a pharmaceutically acceptable salt thereof, $R_1$ is a hydroxyl group, t is 0, $R_2$ is hydrogen, $R_3$ is unsaturated or saturated ($C_1$-$C_{30}$) alkyl, $Q_1$-$R_2$ together is an amine group. More preferably therefore, a sphingolipid used in embodiments of the present invention is a sphingolipid with the general formula (II):

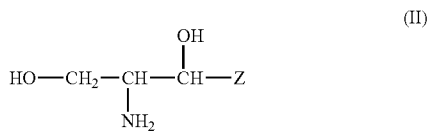

(II)

wherein and Z is $R_3$ or CH(OH)—$R_3$ and $R_3$ is an unsaturated or saturated ($C_1$-$C_{30}$) alkyl chain.

In a most preferred embodiments of the present invention, a phytosphingosine, sphingosine, sphinganine, ceramide, cerebroside and/or sphingomyelin is used, since these compounds show excellent reduction in plasma cholesterol and triglycerides.

Besides sphingomyelin, phytosphingosine, sphingosine, sphinganine, ceramide and cerebroside also derivatives of these compounds may be used in aspects of the present invention. For instance, in stead of a hydroxyl headgroup, a choline phosphate, ethanolamine phosphate, serine phosphate, inositol phosphate, glycerol phosphate, glucose or galactose head group may be used as $R_1$ group in a compound according to the formula (I). Basically all headgroups within the definition of R1 above may be used for derivatization of phytosphingosine, sphingosine and sphinganine. A derivative such as lyso-sphingomyelin may also be used in embodiments of the present invention.

It is also possible to use a combination of sphingolipids according to the formula (I) and/or (II) and/or (III) in aspects of the present invention.

In principle, sphingolipids according to the formula (I) and/or (II) and/or (III) of all possible sources are suitable for use in aspects and embodiments of the present invention. For instance, a suitable sphingolipid such as phytosphingosine may be obtained from plants such as corn (Wright et al., Arch. Biochem. Biophys. 415(2), 184-192 and references therein), from animals (skin fibroblasts) or from microorganisms such as yeasts (such as Pichia ciferii). The sphingolipids may be isolated from these organisms or can be used in a less pure form, i.e. as an enriched fraction, or in the case of microorganisms such as yeasts by taking the complete organism(s) or fractions thereof. Further, sphingolipids may be isolated from other suitable sources, such as from milk, egg, soy, yeast, bacteria, algae, plants, meat, brain, etc. or may be chemically or enzymatically prepared, for use in a pharmaceutical composition or food additive according to the invention.

For application in a food item or food supplement according to the present invention a sphingolipid is preferably derived from a food-grade source. Examples of suitable food-grade sources are e.g. bakery yeast, brewers yeast and egg, and certain types of bacteria, (filamentous) fungi, sponges and algae, in particular, but not exclusively those species of bacteria, yeast and fungi which are generally recognized as safe (GRAS). Bacterial sources of sphingolipids are e.g. known from U.S. Pat. No. 6,204,006.

Sphingolipids may be derived from the above sources by methods known to the skilled person for instance by extraction with (organic) solvents, chromatographic separation, precipitation, crystallization and/or enzymatic of chemical hydrolysis. The production of a sphingolipid-enriched (specifically a sphingomyelin-enriched) fraction from milk is for instance known from WO94/18289. Sphingolipids may also be derived from fat concentrates of various animal products such as milk products, egg products and blood products such as known from U.S. Pat. No. 5,677,472.

Methods for the preparation of sphingolipids and sphingolipid derivatives are i.a. known from EP 0 940 409, WO 98/03529, WO 99/50433 and U.S. Pat. No. 6,204,006 and the artisan will be capable of preparing derivatives by these and other methods. Various routes for obtaining sphingosines are described by D. Shapiro in "Chemistry of Sphingolipids", Hermann, Paris (1969). Methods for producing certain phytosphingolipid derivatives are known to the skilled person, for instance it is known from U.S. Pat. No. 6,204,006 and U.S. Pat. No. 5,618,706 to derive tetraacetyl-phytosphingosine (TAPS) from microbial sources (i.e. Pichia ciferrii) and to subject this TAPS to hydrolysis to yield phytosphingosine.

A sphingolipid according to the formula (I), or a precursor, a derivative or a pharmaceutically acceptable salt thereof, may also be synthesized by known methods such as e.g. known from U.S. Pat. Nos. 5,232,837 and 5,110,987, or by standard modifications of these methods.

A known issue relating to the administration of sphingolipids, be it in foods or in pharmaceutical compositions, is that they can be metabolized. This is particularly relevant for application of sphingolipids in the digestive tract. This issue may be addressed by administering a sphingolipid according to the formula (I), more preferably according to formula (II) or (III), or a derivative or a pharmaceutically acceptable salt thereof, alone or in combination, as a so-called precursor compound which compound comprises certain substituents as a result of which the compound can no longer, or only at reduced rates, be metabolized. These precursors are preferably resistant to hydrolysis in the upper parts of the digestive tract (e.g. mouth, stomach), and are for instance split relatively easy in the lower part of the digestive tract (e.g. coecum, colon), if the sphingolipid should have its working especially there. It is also possible that activation occurs when the compound has been absorbed from the digestive tract, e.g. in the serum or the liver. As a result, the amount of the compound is raised at those locations where the sphingolipid has its action. For instance, a sphingolipid precursor may be used that can be split or activated in vivo by a suitable enzyme so that the sphingolipid is liberated that may reduce the levels of cholesterol and triglycerides in the subject. Sphingolipid precursors have been described in WO 99/41266.

It is possible to modify a precursor of a sphingolipid according to the formula (I), (II) or (III) by an in situ enzymatic or chemical conversion, i.e. in the body, to a sphingolipid according to the formula (I), (II) or (III), which can be used in embodiments of the present invention. Such precursors of a sphingolipid according to the formula (I), (II) or (III) are therefore also suited for use according to the invention. A condition is that the precursor is converted in the body, e.g. preferably in the intestine, to a sphingolipid according to the formula (I), (II) or (III), e.g. by enzymatic conversion, in which case there is in situ activation. It is therefore, for instance possible to administer together with e.g. sphingomyelin, the enzyme sphingomyelin deacylase which may convert the sphingomyelin to lyso-sphingomyelin. Another possibility is to use sphingomyelinase to convert sphingomyelin into ceramide. In its turn ceramide can be broken down by ceramidase into a sphingoid base structure and a fatty acid. Other examples of enzymes may for instance be found in Sueyoshi et al., 1997, J Lipid Res 38:1923-7. Preferably, however, the sphingolipid according to the formula (I), (II) or (III) is not used as a precursor but in its "active" form in a food item or a food supplement or a pharmaceutical preparation.

A sphingolipid according to the formula (I), (II) or (III), or a precursor, a derivative or a pharmaceutically acceptable salt thereof, may be provided to a subject in need thereof for prophylactic or therapeutic reasons. A sphingolipid according to the formula (I), (II) or (II), or a precursor, a derivative or a pharmaceutically acceptable salt thereof, may be provided to a subject in need thereof in the form of a food item or food supplement, or in the form of a pharmaceutical preparation, all such administration forms being capable of lowering the cholesterol and triglyceride levels in a subject. In particular, the levels of cholesterol and triglycerides in the blood plasma and/or serum of said subjects are lowered.

The present invention therefore also relates to a method of lowering cholesterol and triglyceride levels in plasma and/or serum of (healthy) subjects comprising providing said subjects a diet with enhanced levels of a sphingolipid according to formula (I), more preferably according to formula (II), yet more preferably according to formula (III), most preferably phytosphingosine, sphingosine, sphinganine, ceramide, cerebroside or sphingomyelin or a precursor, a derivative or a pharmaceutically acceptable salt thereof. Such a diet comprises the use of food items or food supplements as described herein and the food items and/or food supplements described herein below may suitably represent nutraceuticals as known in the art.

According to current insights a cholesterol serum content of 3-6 mM and contents of triglycerides of less than 2 mM are normal for a healthy human subject. Increased levels do not themselves cause disease, but it is generally accepted that higher levels are a risk factor. In the Examples it is shown that increased levels can be decreased by 50-60% by a diet according to the invention. Such a decrease would suffice to bring elevated levels of cholesterol and/or triglycerides down to levels which do not incur an increased health risk.

A sphingolipid according to the formula (I), more preferably according to formula (II), yet more preferably according to formula (III), or a precursor, a derivative or a pharmaceutically acceptable salt thereof, may be used in a food item or food supplement. A food supplement is defined as a composition that can be consumed in addition to the normal food intake and which comprises elements or components that are not or in only minor amounts, present in the normal diet and of which sufficient or increased consumption is desired. The composition of a food item does not necessarily differ much from that of a food supplement.

A food item or food supplement as disclosed herein comprises an amount of sphingolipids according to the formula (I), (II) or (III) that is higher than the amount that would normally or without human intervention occur or be found in said food item or food supplement. This elevated amount of a sphingolipid according to the formula (I), (II) or (III) may arise through specific addition of said sphingolipid to a food composition that does not normally comprise said sphingolipid in said elevated amount, i.e. by enrichment of the food item with said sphingolipid. Alternatively genetic engineering may be used to produce food products comprising said sphingolipid in an elevated amount, for instance by engineering the biosynthetic routes for the production of such sphingolipids in a plant, or yeast or other microorganism used for the production of a food product in such a way that said sphingolipid is produced in said organism in an elevated amount.

Since amounts of sphingolipids such as phytosphingosine, sphingosine, (lyso-)sphingomyelin or sphinganine may differ considerably between various food items there is no general value for the amount which is said to be an elevated amount or of an enriched food item. In general, milk, which normally contains relatively high amounts of sphingomyelin, is said to comprise an elevated amount at higher absolute concentrations than for instance a potato, which contains no or only minute amounts of sphingomyelin.

A sphingolipid-enriched food item or food supplement as described above may suitably comprise 0.01 to 99.9 wt. % of a sphingolipid according to the formula (I), (II) or (III). In a preferred embodiment such a food item or food supplement comprises from 0.05 to 50 wt. %, preferably from 0.05 to 10 wt. %, more preferably from 0.05 tot 5 wt. % of a sphingolipid according to the formula (I), (II) or (III) or derivatives, precursors or acceptable salts thereof.

In order to make a food item or food supplement comprising an elevated amount a sphingolipid according to the formula (I), (II) or (III) suitable for human or animal consumption, the nutritional value, texture, taste or smell may be improved by adding various compounds to said item or supplement. The skilled person is well aware of the different sources of protein, carbohydrate and fat that may be used in food items or food supplements according to the invention and of the possible sweeteners, vitamins, minerals, electrolytes, coloring agents, odorants, flavoring agents, spices, fillers, emulsifiers, stabilizers, preservatives, anti-oxidants, food fibers, and other components for food items that may be added to improve its nutritional value, taste or texture. The choice for such components is a matter of formulation, design and preference. The amount of such components and substances that can be added is known to the skilled person, wherein the choice may e.g. be guided by recommended daily allowance dosages (RDA dosages) for children and adults and animals.

Portions for intake of the food item or food supplement may vary in size and are not limited to the values corresponding to the recommended dosages. The term "food supplement" is herein not intended to be limited to a specific weight or dosage.

A composition of a food item or food supplement as described above may in principle take any form suited for consumption by man or animal. In one embodiment the composition is in the form of a dry powder that can be suspended, dispersed, emulsified or dissolved in an aqueous liquid such as water, coffee, tea, milk, yogurt, stock or fruit juice and alcoholic drinks. To this end, the powder may be provided in unit-dosage form.

In an alternative preferred embodiment a composition in the form of a dry powder is tabletted. To that end, a composition for a food supplement according to the invention may very suitably be provided with fillers, such as microcrystalline cellulose (MCC) and mannitol, binders such as hydroxypropylcellulose (HPC), and lubricants such as stearic acid or other excipients.

A composition of a food item or food supplement as described above may also be provided in the form of a liquid preparation wherein the solids are suspended, dispersed or emulsified in an aqueous liquid. Such a composition may be admixed directly through a food item or may e.g. be extruded and processed to grains or other shapes.

In an alternative embodiment a food item or food supplement may take the shape of a solid, semi-solid or liquid food item, such as a bar, cookie or a sandwich, spreads, sauces, butter, margarines, dairy products, and the like. Preferably, a cholesterol and triglyceride lowering sphingolipid according to the present invention is applied in a dairy product, such as for instance a butter or margarine, custard, yogurt, cheese, spread, drink, or pudding or other dessert. The sphingolipid can also be used in butters or fats used for frying and baking, because they are relatively stable and will not be degraded by high temperatures. This characteristic also enables use of the sphingolipid in food items or food supplements which undergo a pasteurisation or sterilisation treatment. Diet products also constitute preferred embodiments of food items or food supplements according to the invention.

If a food item according to the invention is used as an animal feed, the food item may e.g. be prepared in the form of a powder, a grain, a waffle, a porridge, a block, a pulp, a paste, a flake, a cook, a suspension or a syrup.

For administration to humans the food substance of the invention may very suitably be prepared in the form of a food supplement.

The present invention further relates to a method for the preparation of a food item or food supplement according to the invention, comprising enriching a food item or food supplement with a sphingolipid according to the formula (I) and/or (II) and/or (III), or a precursor, a derivative or a pharmaceutically acceptable salt thereof.

In one embodiment the invention provides a method for the preparation of a food item or food supplement enriched with a sphingolipid, comprising processing a sphingolipid according to the formula (I), (II) or (III), or a precursor, a derivative or a pharmaceutically acceptable salt thereof in a food item or food supplement, preferably to an amount of 0,01 to 99,9 wt. %, more preferably to an amount of from 0,05 to 50 wt. %, even more preferably to an amount of from 0.05 tot 10 wt. %, and most preferably to an amount of from 0.05 tot 5 wt. %. The amount of sphingolipid processed in a food item according to the invention depends on the type of sphingolipid and its use and the skilled person is capable of determining this amount in the context of the present disclosure.

In a method for preparing a food item according to the invention the food item may first be prepared separately and then be joined with a sphingolipid to provide a food item according to the invention wherein said sphingolipid is incorporated in the food item. The food item may be separately prepared by conventional methods such as by mixing, baking, frying, cooking, steaming or poaching and may, if necessary, be cooled prior to joining with the sphingolipid. According to another suitable embodiment, the sphingolipid is incorporated as a component in the food item during the preparation thereof.

The present invention also relates to a method of treatment of subjects suffering from high plasma cholesterol and triglyceride levels, said method comprising administering to subjects in need thereof a therapeutically effective amount of a pharmaceutical composition, said composition comprising a sphingolipid according to the formula (I), more preferably according to formula (II), yet more preferably according to the formula (III), most preferably phytosphingosine, sphingosine, sphinganine, cerebrosides, ceramide, or sphingomyelin or precursors, derivatives or pharmaceutically acceptable salts thereof and a pharmaceutically acceptable carrier, and optionally one or more excipients.

Dosages for achieving the cholesterol and triglyceride-lowering effects of the pharmaceutical composition, food item or food supplement described herein may easily be determined by the skilled person. For purposes of the present invention, an effective dose will be from about 0.05-5% of the dry food weight in the individual to which it is administered, meaning that for an adult human being the daily dose will be between about 0.01 and 10 grams of sphingolipid.

Preferably a pharmaceutical composition as described above is intended for oral application. Compositions for oral application will usually comprise an inert diluent or an edible carrier. The compositions may be packed in e.g. gelatin capsules or may be tabletted in the form of tablets. For oral therapeutic application the active compound may be administered with excipients and e.g. used in the form of powders, sachets, tablets, pills, pastilles or capsules. Pharmaceutically acceptable binders and/or adjuvants may also be comprised as constituents of the pharmaceutical composition.

The powders, sachets, tablets, pills, pastilles, capsules and such may comprise each of the following components or compounds of similar import: a filler such as microcrystalline cellulose (MCC) or mannitol; a binder such as hydroxypropylcellulose (HPC), tragacanth gum or gelatin; an excipient such as starch or lactose; a desintegrant such as alginate or corn starch; a lubricant such as magnesium stearate; a sweetener such as sucrose or saccharose; or a flavoring substance such as peppermint or methyl salicylic acid.

When dosing is in the form of a capsule, the capsule may comprise apart from the elements mentioned above a liquid carrier such as an oil. Dosage form may further be provided with coatings of sugar, shellac or other agents. The components of the pharmaceutical composition are preferably chosen such that they do not reduce the desired working of the sphingolipid.

A sphingolipid according to the formula (I), (II) or (III) or the pharmaceutically acceptable salt thereof may also be administered in the form of e.g. an elixir, a suspension, a syrup, a waffle or a chewing gum.

In a pharmaceutical composition as described above, a sphingolipid according to the formula (I), (II) or (III), or a precursor, a derivative or a pharmaceutically acceptable salt thereof, is used in an amount of from 0.01 to 99.9% by weight, preferably from 0.01 to 10 wt. %, and more preferably from 0.05 to 1 wt. %.

A pharmaceutical composition according to the invention is intended for reducing both the cholesterol and triglyceride levels of a subject, preferably the subject's plasma levels.

The present invention further relates to a method for the preparation of a pharmaceutical composition for reducing cholesterol and triglyceride levels in a subject, comprising processing or incorporating a sphingolipid according to the formula (I), (II) or (III), or a precursor, a derivative or a pharmaceutically acceptable salt thereof, as an active substance, together with a pharmaceutically acceptable carrier in a pharmaceutical composition.

The preparation of a pharmaceutical composition may very suitably occur by mixing all separate ingredients such as fillers, binders, lubricants and optionally other excipients together with a sphingolipid according to the formula (I), (II) or (III) or a precursor, a derivative or a pharmaceutically acceptable salt thereof, and processing the mixture obtained to a pharmaceutical preparation.

The invention will now be illustrated by way of the following, non-limiting examples.

EXAMPLES

Example

Effect of Sphingolipids in Transgenic APOE*3Leiden Mice Fed a "Western-Type" Diet In this experiment mice were used in which the human gene for the so-called Leiden mutation of apolipoprotein E3 (APOE*3Leiden transgenic mice) had been incorporated by transgenesis. Because of this transgenic change, these so-called APOE*3Leiden mice have a humanized lipoprotein profile, and are extremely suitable for studying the effect of compounds on lipoprotein metabolism (Van Vlijmen et. al. 1996. J Clin Invest. 97:1184-1192; Van Vlijmen et. al. 1998. Arzneimittelforschung 1998; 48:396-402.).

The study design was as follows: female mice were fed for 5 weeks "Western-type" diet (Nishina et al. 1990. J Lipid Res. 31:859-869) containing 0.25% (w/w) cholesterol. Specifically, the diet contained 15% (all w/w) cocoabutter, 0.25% cholesterol, 1% corn oil, 40.5% sucrose, 20% acid casein, 10% corn starch and 5.95% cellulose, as major ingredients. This diet increased their plasma cholesterol level to about 15 mmol/L. Subsequently, the mice were randomized, on the basis of their plasma cholesterol level, into groups of six mice each. These groups were given the same diet, but containing in addition:
Group 1 no addition
Group 2 0.1% (w/w) phytosphingosine
Group 3 0.1% (w/w) sphingosine
Group 4 0.1% (w/w) sphinganine
Group 5 0.1% (w/w) cerebroside
Group 6 0.1% (w/w) ceramide IV
Group 7 0.1% (w/w) sphingomyelin The phytosphingosine, ceramide IV and cerebroside (=glucosyl ceramide) were obtained from Cosmoferm BV (Delft, The Netherlands). Sphingomyelin from egg was obtained from Larodan Fine Chemicals AB (Stockholm, Sweden) and sphingosine and sphinganine were obtained from Avanti Polar Lipids Inc, (Alabaster, Ala., USA). During the experiment, body weight and food intake were monitored. At three weeks after the dietary change, blood was taken to determine plasma cholesterol and triglyceride levels. Also, the plasma lipoprotein pattern was determined group wise in pooled samples by fplc. Then, the concentration of the additives was changed to 0.2%, and feeding continued for another 3 weeks. At three weeks after this dietary change, blood was again taken to determine plasma cholesterol and triglyceride levels, and the plasma lipoprotein pattern was determined group wise in pooled samples by fplc. The dietary additives were then changed to 0.4% (w/w), and the same cycle of feeding and blood sampling was executed.

In the groups 2-7, both plasma cholesterol and triglycerides were reduced, as shown in detail in FIGS. 1-6, and in Tables 1 and 2.

Figure 7:
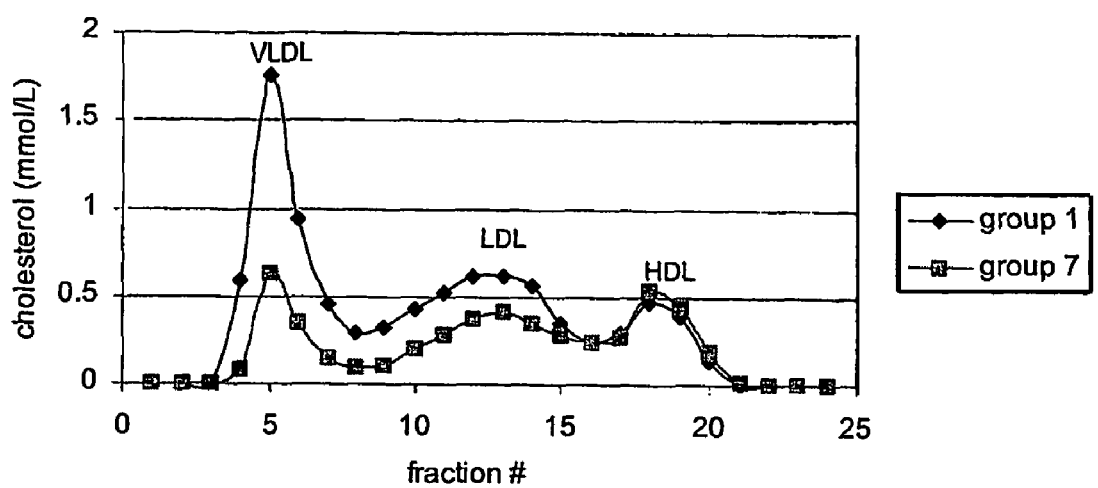
FIG. 7 shows the pattern of the distribution of cholesterol over the lipoprotein fractions in group 1 (control group) and in group 7 (sphingomyelin administered at 0.4%), as determined after separation by fplc (AKTA system).
Figure 8:
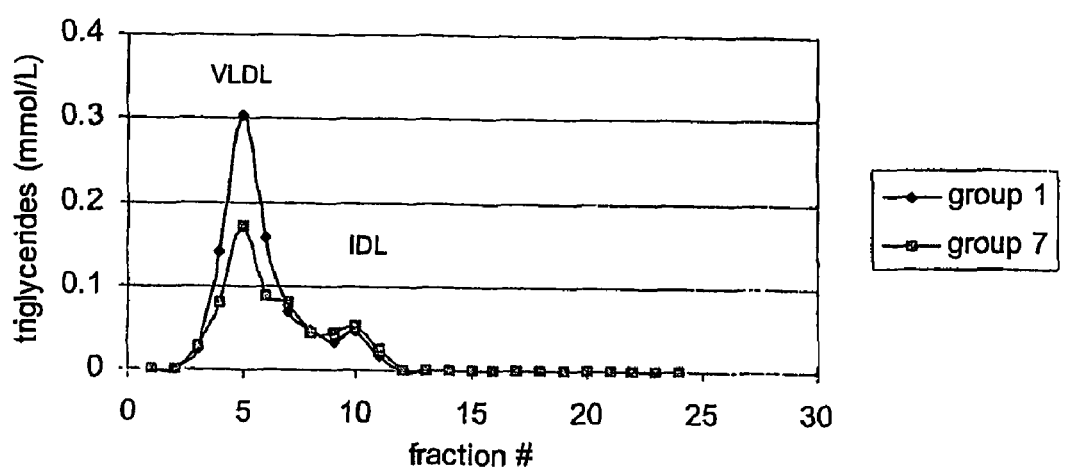
FIG. 8 shows the pattern of the distribution of triglycerides over the lipoprotein fractions in group 1 (control group) and in group 7 (sphingomyelin administered at 0.4%), as determined after separation by fplc (AKTA system).

Analysis of the lipoprotein distribution pattern in plasma from mice of groups 2-7 by fplc showed that the decrease in cholesterol and triglycerides was due to a decrease in the VLDL and IDL/LDL fractions, and not in the HDL fraction (see FIGS. 7 en 8).

Plasma alanine aminotransferase (ALAT) activity was decreased in all groups, indicating that liver function was not affected (Table 3).

In a separate experiment, groups of six APOE*3Leiden mice were fed the above-described Western-type diet, containing 1.0% (w/w) of phytosphingosine. At the end of the treatment period, plasma cholesterol was reduced with 58% (p=0.007) and plasma triglyceride was reduced with 64% (p=0.01) with respect to the control group. By fplc analysis it was determined that the decrease of cholesterol and triglycerides was fully due to a decrease in VLDL and IDL/LDL fractions.

No significant differences in the body weights of the mice, the food intake per day or in the weights of the livers of the mice was found as a result of the presence in the food of the 6 sphingolipids tested.

TABLE 1

Plasma cholesterol levels

| | t = 0 mmol/L | t = 3 (0.1%) mmol/L | t = 6 (0.2%) mmol/L | t = 9 (0.4%) mmol/L |
|---|---|---|---|---|
| 1 = CONTROL | 14.6 | 15.0 | 15.7 | 16.7 |
| 2 = PHYTOSPHINGOSINE | 14.4 | 13.2 | 12.6 | 10.9 |
| 3 = SPHINGOSINE | 14.6 | 15.3 | 11.0 | 9.5 |
| 4 = SPHINGANINE | 15.9 | 14.9 | 10.0 | 11.5 |
| 5 = CEREBROSIDE | 14.8 | 14.2 | 11.7 | 12.8 |
| 6 = CERAMIDE | 15.6 | 14.8 | 12.6 | 11.7 |
| 7 = SPHINGOMYELIN | 15.1 | 14.7 | 9.9 | 8.7 |

| | t = 0 | t = 3 (0.1%) reduction relative to control (%) | t = 6 (0.2%) reduction relative to control (%) | t = 9 (0.4%) reduction relative to control (%) |
|---|---|---|---|---|
| 1 = CONTROL | | | | |
| 2 = PHYTOSPHINGOSINE | | 11.6 | 19.7 | 34.8 |
| 3 = SPHINGOSINE | | -2.1 | 29.7 | 43.3 |
| 4 = SPHINGANINE | | 0.3 | 36.2 | 31.2 |
| 5 = CEREBROSIDE | | 5.2 | 25.6 | 23.4 |
| 6 = CERAMIDE | | 1.5 | 19.4 | 29.9 |
| 7 = SPHINGOMYELIN | | 1.9 | 36.8 | 48.2 |

TABLE 2

Plasma triglyceride levels

| | t = 0 mmol/L | t = 3 (0.1%) mmol/L | t = 6 (0.2%) mmol/L | t = 9 (0.4%) mmol/L |
|---|---|---|---|---|
| 1 = CONTROL | 2.4 | 2.1 | 2.1 | 2.3 |
| 2 = PHYTOSPHINGOSINE | 2.1 | 1.7 | 1.2 | 1.5 |
| 3 = SPHINGOSINE | 2.3 | 2.2 | 1.4 | 1.0 |
| 4 = SPHINGANINE | 2.3 | 1.7 | 1.0 | 1.2 |
| 5 = CEREBROSIDE | 2.2 | 2.2 | 1.2 | 1.8 |
| 6 = CERAMIDE | 2.3 | 2.0 | 1.1 | 1.4 |
| 7 = SPHINGOMYELIN | 2.5 | 1.7 | 1.2 | 0.9 |

| | t = 0 | t = 3 (0.1%) reduction relative to control (%) | t = 6 (0.2%) reduction relative to control (%) | t = 9 (0.4%) reduction relative to control (%) |
|---|---|---|---|---|
| 1 = CONTROL | | | | |
| 2 = PHYTOSPHINGOSINE | | 22.9 | 39.8 | 34.8 |
| 3 = SPHINGOSINE | | -0.6 | 32.5 | 54.3 |
| 4 = SPHINGANINE | | 19.2 | 52.9 | 44.9 |

TABLE 2-continued

| | Plasma triglyceride levels | | |
|---|---|---|---|
| 5 = CEREBROSIDE | −1.2 | 42.0 | 21.9 |
| 6 = CERAMIDE | 8.5 | 49.1 | 38.4 |
| 7 = SPHINGOMYELIN | 19.9 | 42.7 | 59.5 |

TABLE 3

Plasma ALAT levels
ALAT(U/L)

| | t = 0 Units/liter | t = 3 (0.1%) Units/liter | t = 6 (0.2%) Units/liter | t = 9 (0.4%) Units/liter |
|---|---|---|---|---|
| 1 = CONTROL | 81.6 | 62.2 | 66.5 | 63.8 |
| 2 = PHYTOSPHINGOSINE | 86.8 | 59.6 | 43.2 | 46.3 |
| 3 = SPHINGOSINE | 92.5 | 73.7 | 39.6 | 39.9 |
| 4 = SPHINGANINE | 89.7 | 77.4 | 54.5 | 65.8 |
| 5 = CEREBROSIDE | 79.9 | 73.7 | 57.5 | 62.6 |
| 6 = CERAMIDE | 96.8 | 97.3 | 86.0 | 85.1 |
| 7 = SPHINGOMYELIN | 74.4 | 67.6 | 46.5 | 44.7 |

The invention claimed is:

1. Method of treatment of a subject having high plasma or serum cholesterol and high triglyceride levels, said method comprising:
   administering to said subject a therapeutically effective amount of a food item, said food item enriched with a plasma or serum cholesterol and triglyceride lowering agent consisting essentially of a sphingolipid according to the formula (I):

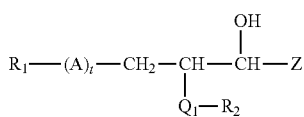

wherein
   Z is $R_3$ or —CH(OH)—$R_3$,
   A is sulphate, sulphonate, phosphate, phosphonate or —C(O)O—,
   $R_1$ is H, hydroxyl, alditol, aldose, an alcohol, $C_1$-$C_6$ alkyl, or an amino acid,
   $R_2$ is H or an unsaturated or saturated ($C_1$-$C_{30}$) alkyl chain,
   $R_3$ is an unsaturated or saturated ($C_1$-$C_{30}$) alkyl chain,
   $Q_1$ is a primary amine group (—$NH_2$), secondary amine group (—NH—) or an amide group (—NH—CO—), and
   t is 0 or 1, or a pharmaceutically acceptable salt thereof and a pharmaceutically acceptable carrier, and optionally one or more excipients;
   determining, after said administering, a plasma or serum cholesterol level in said subject; and
   determining, after said administering, a plasma or serum triglyceride level in said subject.

2. The method of claim 1, wherein said sphingolipid is selected from the group consisting of phytosphingosine, sphingosine, sphinganine, ceramide, cerebroside, sphingomyelin, and lysosphingomyelin.

3. The method of claim 1, wherein the sphingolipid is present in an amount from 0.05 to 50 wt %.

4. The method of claim 3, wherein the sphingolipid is present in an amount from 0.05 to 10 wt %.

5. The method of claim 4, wherein the sphingolipid is present in an amount of from 0.05 to 5 wt %.

6. The method of claim 1, wherein the food item is a dairy product.

7. Method of treatment of a human subject having high plasma or serum cholesterol and high triglyceride levels, said method comprising:
   administering to said subject a therapeutically effective amount of a pharmaceutical composition or a food supplement, said composition or supplement comprising a plasma or serum cholesterol and triglyceride lowering agent according to the formula (I):

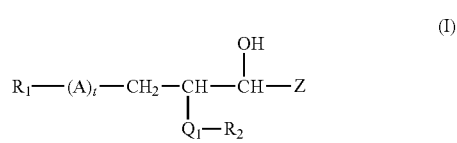

wherein
   Z is $R_3$ or —CH(OH)—$R_3$,
   A is sulphate, sulphonate, phosphate, phosphonate or —C(O)O—,
   $R_1$ is H, hydroxyl, alditol, aldose, an alcohol, $C_1$-$C_6$ alkyl, or an amino acid,
   $R_2$ is H or an unsaturated or saturated ($C_1$-$C_{30}$) alkyl chain,
   $R_3$ is an unsaturated or saturated ($C_1$-$C_{30}$) alkyl chain,
   $Q_1$ is a primary amine group (—$NH_2$), secondary amine group (—NH—) or an amide group (—NH—CO—), and
   t is 0 or 1, or a pharmaceutically acceptable salt thereof and a pharmaceutically acceptable carrier, and optionally one or more excipients;
and wherein said agent is administered at a daily dose in the range of 10 mg to 10 g;
   determining, after said administering, a plasma or serum cholesterol level in said subject; and
   determining, after said administering, a plasma or serum triglyceride level in said subject.

8. The method of claim 1 or claim 7, further comprising:
   determining, prior to said administering, a plasma or serum cholesterol level in said subject;
   determining, prior to said administering, a plasma or serum triglyceride level in said subject; and
   comparing the plasma or serum cholesterol and triglyceride levels determined prior to and after said administering, wherein administering said agent lowers both cholesterol and triglyceride levels in plasma or serum of said subject.

9. The method of claim 8, wherein the step of administering is performed on an ongoing basis, and the steps of determining are performed after three weeks, six weeks, or nine weeks of administering.

10. The method of claim 1 or claim 7, wherein the step of administering is performed on an ongoing basis.

11. The method of claim 7, wherein the sphingolipid is present in an amount from 0.05 to 50 wt %.

12. The method of claim 11, wherein the sphingolipid is present in an amount from 0.05 to 10 wt %.

13. The method of claim 12, wherein the sphingolipid is present in an amount of from 0.05 to 5 wt %.

14. The method of claim 7, wherein a food supplement is administered, and the food supplement is a dairy product.

* * * * *